United States Patent
Al-Hazmi

(10) Patent No.: US 10,526,275 B2
(45) Date of Patent: *Jan. 7, 2020

(54) MINIMIZING WATER CONTENT IN ETHANOLAMINE PRODUCT STREAMS

(71) Applicant: SABIC GLOBAL TECHNOLOGIES B.V., Bergen op Zoom (NL)

(72) Inventor: Naeem Al-Hazmi, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/302,600

(22) PCT Filed: Apr. 6, 2015

(86) PCT No.: PCT/IB2015/052483
§ 371 (c)(1),
(2) Date: Oct. 7, 2016

(87) PCT Pub. No.: WO2015/155667
PCT Pub. Date: Oct. 15, 2015

(65) Prior Publication Data
US 2017/0022145 A1    Jan. 26, 2017

Related U.S. Application Data

(60) Provisional application No. 61/976,836, filed on Apr. 8, 2014.

(51) Int. Cl.
*C07C 213/04*    (2006.01)
*B01D 3/14*    (2006.01)
(Continued)

(52) U.S. Cl.
CPC ............ *C07C 213/04* (2013.01); *B01D 3/143* (2013.01); *B01D 3/322* (2013.01); *C07C 213/10* (2013.01)

(58) Field of Classification Search
None
See application file for complete search history.

(56) References Cited

U.S. PATENT DOCUMENTS

| 2,823,236 A | 2/1958 | Lowe et al. |
| 3,453,183 A | 7/1969 | Okubo et al. |

(Continued)

FOREIGN PATENT DOCUMENTS

| CA | 2542546 A1 | 6/2005 |
| CN | 103772211 A | 5/2014 |

(Continued)

OTHER PUBLICATIONS

Merluzzi, P. et al., "Nearly Optimal Control of a Pilot Plant Distillation Column", AIChE Journal, 1972, vol. 18, No. 4, pp. 739-744.

(Continued)

*Primary Examiner* — Clinton A Brooks
(74) *Attorney, Agent, or Firm* — Norton Rose Fulbright US LLP

(57) ABSTRACT

Systems and method are provided for reducing the water content in ethanolamine product streams from approximately 0.15%-0.19% by weight of water to approximately 0.02 to approximately 0.04 by weight of water. The reduced water content can be achieved by increasing the processing conditions at the monoethanolamine column by approximately 5% to approximately 20%, more preferably to approximately 10%, and by adding a dummy stream to the monoethanolamine column, which can be recycled to the reactor. The increased processing conditions and dummy stream at the monoethanolamine column can result in the following to achieve said water content: (i) the bottom stream flow rate increase by up to approximately 18.9%; the reboiler duty can be increased by up to 47.9%; and (iii) the condenser duty can be increased by up to approximately 52.5%.

19 Claims, 2 Drawing Sheets

(51) Int. Cl.
  *B01D 3/32*  (2006.01)
  *C07C 213/10*  (2006.01)

(56) References Cited

U.S. PATENT DOCUMENTS

| | | | |
|---|---|---|---|
| 3,849,262 | A | 11/1974 | Cocuzza |
| 4,169,856 | A | 10/1979 | Cocuzza et al. |
| 4,355,181 | A | 10/1982 | Willis, Jr. et al. |
| 5,545,757 | A | 8/1996 | Hammer et al. |
| 6,323,371 | B2 | 11/2001 | Ruider et al. |
| 6,696,610 | B2 | 2/2004 | Preschel et al. |
| 6,846,959 | B2 | 1/2005 | Garg et al. |
| 7,164,044 | B2 | 1/2007 | Morishita et al. |
| 7,550,632 | B2 | 6/2009 | Haese et al. |
| 7,560,594 | B2 | 7/2009 | Haese et al. |
| 8,466,323 | B2 | 6/2013 | Melder et al. |
| 2002/0123653 | A1* | 9/2002 | Tsuneki ............... B01J 8/025 564/475 |
| 2006/0293541 | A1 | 12/2006 | Reif et al. |
| 2014/0061020 | A1 | 3/2014 | Schmidt et al. |
| 2017/0174616 | A1* | 6/2017 | Al-Hazmi ............ C07C 215/08 |

FOREIGN PATENT DOCUMENTS

| | | |
|---|---|---|
| EP | 0690043 A2 | 1/1996 |
| EP | 2177501 A1 | 4/2010 |
| GB | 1092449 A | 11/1967 |
| IN | 238069 | 7/2007 |
| JP | 2004238290 A | 8/2004 |
| WO | 0153250 A1 | 7/2001 |
| WO | 2004113268 A1 | 12/2004 |
| WO | 2015151057 A1 | 10/2015 |
| WO | 2015181748 A1 | 12/2015 |
| WO | 2015181751 A1 | 12/2015 |

OTHER PUBLICATIONS

International Search Report for International Application No. PCT/IB2015/052483; dated Jun. 23, 2015; 4 Pages.
Japanese Patent No. 2004238290; Date of Publication: Aug. 26, 2004; Abstract Only, 2 pages.
Tsuneki, H., "Development of Diethanolamine Selective Production Process Using Shape-Selective Zeolite Catalyst"; Catalysis Surveys Asia, 2010, vol. 14, pp. 116-123.
Written Opinion of the International Search Report for International Application No. PCT/IB2015/052483; dated Jun. 23, 2015; 7 Pages.
Chinese Patent No. 103772211; Date of Publication: May 7, 2014; Abstract Only, 2 pages.

\* cited by examiner

US 10,526,275 B2

MINIMIZING WATER CONTENT IN ETHANOLAMINE PRODUCT STREAMS

CROSS REFERENCE TO RELATED APPLICATIONS

This application is a 371 of International Application No. PCT/IB2015/052483, filed Apr. 6, 2015, which claims priority to U.S. Application No. 61/976,836, filed Apr. 8, 2014 both which are incorporated herein by reference in their entirety.

TECHNICAL FIELD

The present invention relates to a process for the production of ethanolamines, specifically, to a process for minimizing the water content in ethanolamine product streams, such as a monoethanolamine ("MEA") product stream.

BACKGROUND

Ethanolamines, individually and in combination have many uses in the chemical industries. For example, ethanolamines can be used as corrosion inhibitors, lubricants and scouring agents for gas sweetening, detergents and specialty cleaners, concrete admixtures, flexible urethane foam catalysts, personal care products, photographic emulsions, solvents, dyes intermediates, rubber accelerator, emulsifiers, ink additives, oil additives, alkalization of water in steam cycles of power plants and nuclear plants with pressurized water reactors, pesticides and pharmaceutical intermediates, natural gas is also used as acid gas absorption solvent. Ethanolamines can also be used in the semiconductor field for wafer cleaning and photoresist striping applications because of their surfactant properties. Global demand for ethanolamines is increasing, and is projected to exceed 1.605 million tons by 2015.

Ethanolamines are flammable, corrosive, colorless, viscous liquids that are produced by the reaction of ammonia ($NH_3$) and halohydrins or ethylene oxide ($C_2H_4O$) (EO). EO, however, is more widely used for commercial processes. To produce ethanolamines commercially, aqueous ammonia and ethylene oxide are contacted in a single stage or multi-stage reaction chamber at a temperature within the range of 50° C. to 257° C. There are three types of ethanolamines: MEA ($H_2NCH_2CH_2OH$); Diethanolamine ($HN(CH_2CH_2OH)_2$), also referred to as DEA; and Triethanolamine ($N(CH_2CH_2OH)_3$), also referred to as TEA. The formation of MEA, DEA or TEA depends on whether an ammonia molecule reacts with 1, 2 or 3 EO molecules. The reactions have a parallel consecutive mechanism, so that the three products (MEA, DEA and TEA) are obtained simultaneously. Water is used as a catalyst in ethanolamine reaction.

Due to the demand for ethanolamines in the petrochemical industry, needs exist for producing higher-yield ethanolamine product streams via a cost-effective process.

SUMMARY

Embodiments of the present invention can include a system and method for producing an ethanolamine product stream in a non-reactive distillation column. The method can include: mixing an ammonia solution containing approximately 30% to approximately 40% by weight ammonia with ethylene oxide in a reactor to create a resultant product stream, wherein said resultant product stream includes ethanolamines, unreacted ammonia and water; removing approximately 30% to approximately 50% by weight of the unreacted ammonia and approximately 50% to approximately 70% by weight of water from the resultant product stream to create a stripped product stream, wherein the stripped product stream includes ethanolamines and approximately 30% to approximately 50% by weight of water; transferring the stripped product stream to at least one stage of a vacuum drying column to create a dehydrated product stream; transferring the dehydrated product stream to at least one stage of a monoethanolamine distillation column to create a distilled product stream, wherein the dehydrated product stream includes ethanolamines and approximately 0.01% to approximately 0.1% by weight of water; operating the monoethanolamine distillation column at adjusted processing conditions, wherein said processing conditions are selected from the dehydrated product stream flow rate, reflux rate at the monoethanolamine distillation column, condenser heat duty at the monoethanolamine distillation column, reboiler heat duty at the monoethanolamine distillation column, bottom rate at the monoethanolamine distillation column or a combination comprising at least one of the foregoing, and wherein said processing conditions are approximately 5% to approximately 20% above a base case value of the selected processing conditions; removing a portion of the water from the distilled product stream via a dummy stream to create an ethanolamine product stream, wherein said ethanolamine product stream includes ethanolamines and approximately 0.02% to approximately 0.04% by weight of water.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings like elements are numbered alike and are presented for the purposes of illustrating the exemplary embodiments disclosed herein and not for the purposes of limiting the same.

DETAILED DESCRIPTION

Embodiments of the present invention can provide an improved process for minimizing the water content in ethanolamine product streams from distillation columns in a non-reactive distillation apparatus. This invention can be practiced over a wide range of processing conditions, including, but not limited to the concentrations of reactants, flow rates of reactants, temperatures, and pressures. The process 100 can be conducted in the presence or absence of a catalyst, wherein the catalyst is preferably water. The process 100 can be conducted in aqueous or non-aqueous phase. A desired output product in the process 100 can be manipulated to contain various ratios of MEA, DEA, and TEA by selecting appropriate processing conditions. The process as described herein are exemplary processes only and used for illustrative purposes. Other variations and combinations of steps and components can be used as necessary.

Figure 1:
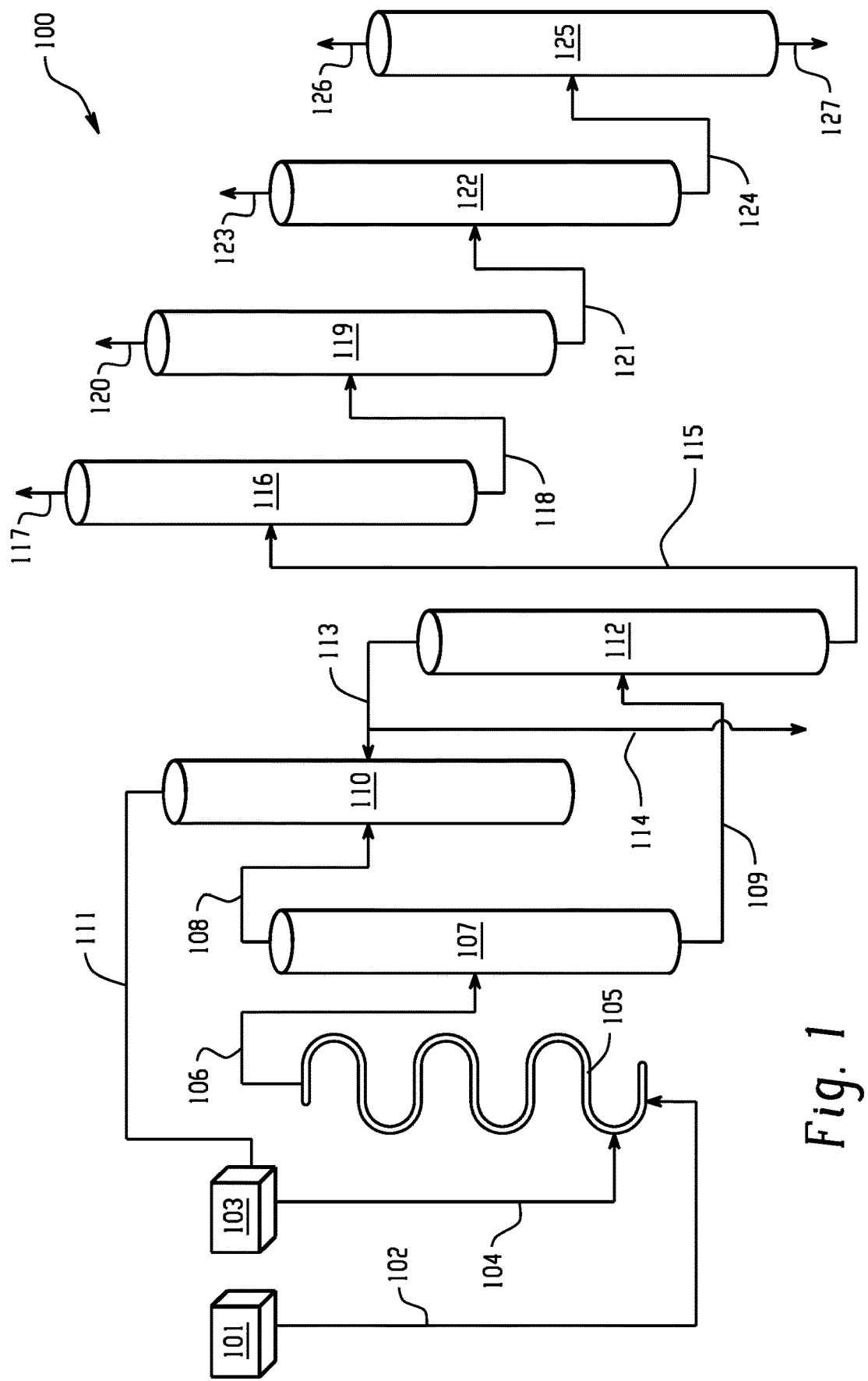
FIG. 1 is a schematic representation of an ethanolamine production process according to one embodiment.

Now referring to FIG. 1, there is shown a schematic representation of an ethanolamine production process according to one embodiment. The process 100 can include a reactor 105, in which EO can be reacted with excess ammonia and water in an aqueous solution to form an ethanolamine reaction product containing MEA, DEA and TEA; an ammonia stripper 107 for stripping the unreacted ammonia from the reaction product and for removing the excess ammonia and some water by distillation; a vacuum drying column 112 for evaporating water from the stripped reaction product to create a dehydrated reaction product; and an amine distillation component for separating the dehydrated reaction product into MEA, DEA and TEA. In some alternatives, the process 100 can also include an ammonia absorber 110 and ammonia solution storage 103 for recycling the excess ammonia stripped from the reaction product, which can be fed to the reactor 105 through line 104. Ammonia solution storage 103 can also be fed to ammonia absorber 110 through line 111. In some alternatives, the process 100 can also include EO storage 101. In some alternatives, the ammonia striper 107, the drying column 112, and the distillation or splitter columns can be carried out with one or more plate-type columns. In some alternatives, the one or more plate-type columns can include a reaction zone (top section) and a stripping zone (bottom section). In some alternatives, the columns can include multiple plates or stages, for example, from approximately 5 to approximately 20 stages. The reactor 105 used in the process 100 can be an isothermal reactor, an adiabatic reactor or other known reactor. A tubular reactor externally cooled by circulating water can preferably be used. In some alternatives, the length of the reactor 105 can range from approximately 2 meters to approximately 35 meters. In some alternatives, the diameter of the reactor 105 can range from approximately 0.2 meters to approximately 0.5 meters.

The invention will be illustrated in more detail with reference to the following examples, but it should be understood that the present invention is not deemed to be limited thereto. Unless otherwise stated, all examples were based upon simulations.

EXAMPLES

Example 1

Base Case at MEA Column 116

A simulation model can be developed to evaluate components of the process 100 including the water content of the ethanolamine product streams. The model can be developed using Aspen™ simulation software (Aspen Plus™ and Aspen Custom Modeler™) or other simulation software, such as Simulation Sciences (SimSci) Pro/II™. The model can be validated against actual plant behavior. Data from actual plant behavior can be input into the model and can be used to tweak the model. The model can use data from processing conditions, e.g., at a plant in Saudi Arabia, capable of producing approximately 90,000-110,000 tons of ethanolamine per year. The plant can also be capable of producing approximately 700,000 tons of Mono-ethylene glycol (MEG) per year. In some alternatives, the model can be developed with Oxiteno process flow diagram (PFD) data for the ethanolamine production process. These simulations can be labeled as the base case.

Figure 2:
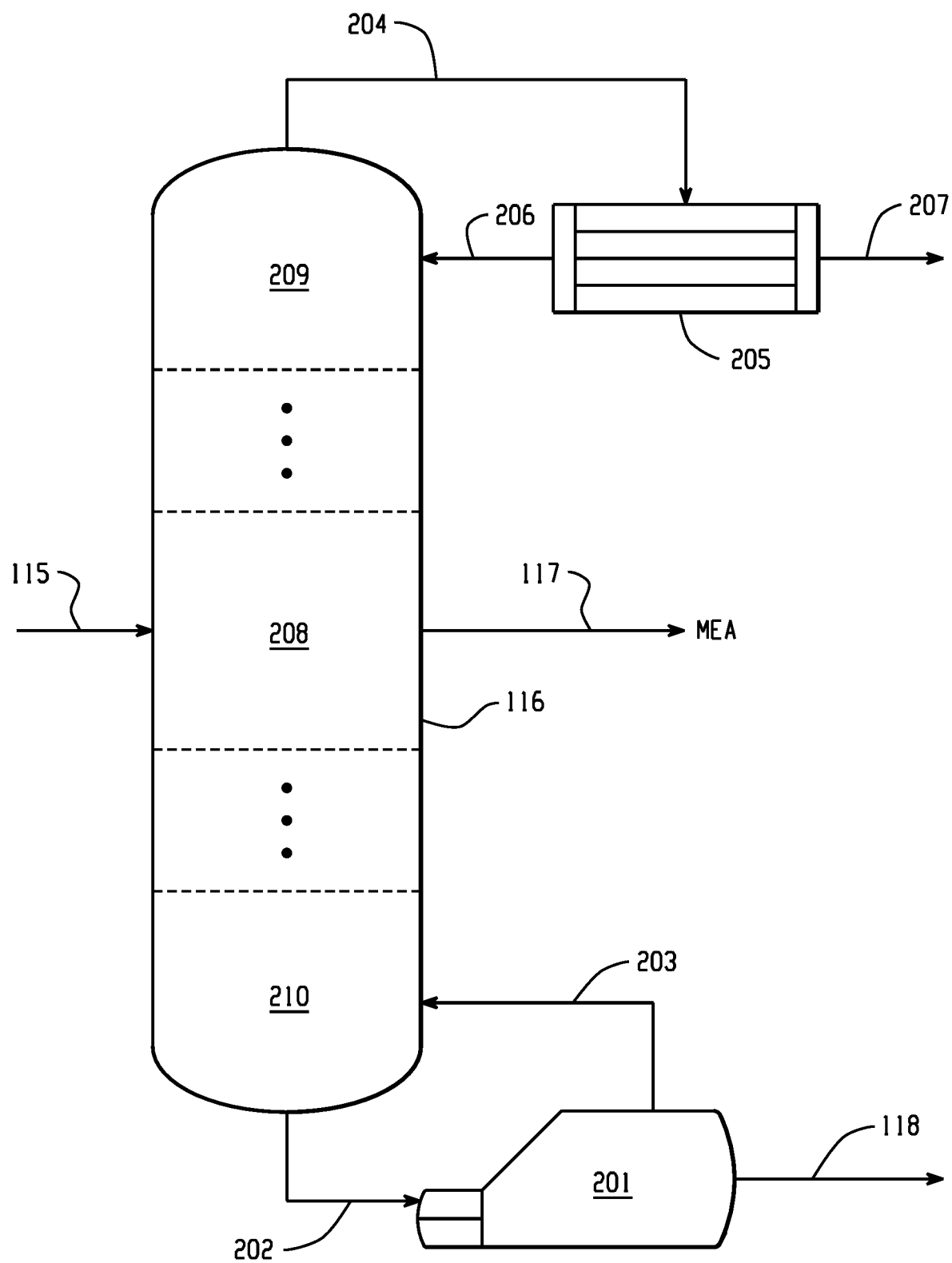
FIG. 2 illustrates an ASPEN™ simulation of a monoethanolamine column according to one embodiment.

Now referring to FIGS. 1 and 2, there is shown an ASPEN™ simulation of a monoethanolamine column according to one embodiment. The process 100 can utilize six stages of tubular reactors 105 connected in series with intercoolers between the reactors 105. In some alternatives, the intercoolers can consist of a bundle of U-tubes, maintained at temperatures from approximately 37° C. to approximately 70° C. More preferably, the temperatures of the U-tubes can be maintained at temperatures from approximately 41° C. -43° C. to approximately 60° C.-63° C. The temperature at the tubular reactors 105 can be cooled down from approximately 60° C.-63° C. at the outlet of each stage of the tubular reactors 105 to approximately 41° C.-43° C., where it can be fed to the inlet of each stage of the tubular reactors 105 by means of an intercooler using a circulating or evaporating coolant as the cooling media. In some alternatives, the coolant can be water.

An aqueous ammonia feed from ammonia storage 103 can be introduced to the first stage of the reactor via line 104. An alkylene oxide, such as EO, from EO storage 101 can also be introduced to the first stage of the reactor 105 via line 102. In some alternatives, the ammonia feed from ammonia storage 103 and the EO feed from EO storage 101 can be combined before being introduced to the first stage of the reactor 105. In some alternatives, the aqueous ammonia solution can include approximately 30-40% by weight of ammonia and 50-70% by weight of water.

More preferably, the ammonia solution can include approximately 33-35% by weight of ammonia and approximately 62% by weight of water. In some alternatives, the % by weight of ammonia can be maintained below 50% to increase the production of MEG. In some alternatives, the ethanolamines produced by the process 100 can be recycled back into reactor 105 to adjust the desired MEA:DEA:TEA ratio. In some alternatives, approximately 1-5% by weight of MEA can be added to the aqueous ammonia solution. In some alternatives, approximately 1-5% by weight of DEA can be added to the aqueous ammonia solution. More preferably, approximately 2.7% by weight MEA and approximately 2.2% by weight DEA can also be added to the aqueous ammonia solution. In some alternatives, the ammonia in the aqueous ammonia solution can be freshly added ammonia, recycled ammonia, or combinations comprising at least one of the foregoing. In some alternatives, the fresh ammonia can be fed directly into a reactor 105 or at some other point in the process 100 (e.g., to the ammonia stripper 107). In some alternatives, ammonia suitable for the reaction can be anhydrous or a solution of ammonia and water.

In some alternatives, the required EO for the reaction can be split evenly across the stages of the reactor 105. The flow of EO to each stage of the reactor 105 via line 102 can be maintained from approximately 1,500 kilograms per hour (kg/hr) to approximately 1,800 kg/hr. More preferably, the flow of EO to each stage of the reactor 105 can be maintained at 1,714.2 kg/hr to produce the desired EO conversion at the outlet of each stage of the reactor 105. In some alternatives, the EO flow rate to each stage of the reactor 105 can be one sixth of the total EO flow rate for line 102, for example, one-sixth of a total EO flow rate of 10,285 kg/hr.

The flow rate of the EO can ensure that approximately eighty-six percent of the EO can be converted in the reactions occurring at the first four stages of the reactor 105. Approximately ninety-nine percent of the EO can be converted in the reaction occurring at the fifth stage of the reactor 105 and greater than ninety-nine percent of the EO can be converted in the reaction occurring at the sixth stage of the reactor 105. In some alternatives, the EO flow rate to each stage of the reactor 105 can depend on the production rate of the ethanolamines. The pressure at each stage of the reactor 105 can be maintained at approximately 15 barg to approximately 30 barg. More preferably, the pressure at each stage of the reactor 105 can be maintained at approximately 19 barg to approximately 24 barg, to avoid the evaporation of EO and ammonia. The reactions in the reactor 105 can form a reaction product effluent, which can contain ethanolamines, unreacted/excess ammonia, any other unreacted components (e.g., water and the like), and optionally one or more reaction by-products, such as MEG.

The resultant product stream can be introduced via line 106 above the fourth stage of the ammonia stripper 107, which can contain approximately sixteen stages. The feed rate for line 106 can be at approximately 58,170 kg/hr to approximately 58,190 kg/hr. More preferably, the feed rate can be 58,180 kg/hr. The ammonia stripper 107 can remove the excess or unreacted ammonia from the reaction product effluent. The ammonia stripper 107 can operate at a pressure of approximately 1 barg to approximately 5 barg, and more preferably, approximately 3.5 barg to approximately 3.6 barg. A flow, which can include approximately 35-45% by weight ammonia and 40-60% by weight of water, negligible quantities of ethanolamines and MEG can be collected from the head of the ammonia stripper 107 via line 108 and conveyed to an ammonia absorber 110. More preferably, the flow can include approximately 40% by weight of unreacted ammonia, approximately 59% by weight of water, negligible quantities of ethanolamines and MEG. The overhead vapors of the ammonia stripper 107 can be cooled and condensed and then fed to an ammonia absorption column 110 via line 108. Fresh ammonia makeup can be fed into the ammonia absorption column 110 and both streams can form part of the aqueous ammonia feed to the reactor 105 via line 104. The temperature at the top of the ammonia stripper 107 can be approximately 130° C. to approximately 140° C., and more preferably approximately 133.6° C. to approximately 135.2° C. A second flow containing ethanolamines, byproducts and the remaining water can be extracted at the foot of the ammonia stripper 107 via line 109 and fed to drying column 112 where a dehydrated mixture of ethanolamines can be obtained by the evaporation of the remaining water. The temperature at the foot of the ammonia stripper 107 can be approximately 150° C. to approximately 165° C., and more preferably approximately 158.2° C. to approximately 159.6° C. The second flow can contain approximately 35-50% by weight water, and more preferably, approximately 40-43% by weight of water. In some alternatives, part of the flow collected from the head of the ammonia stripper 107 via line 108, which can include approximately 90-99% by weight of water and negligible quantities of ethanolamine can be refluxed into the drying column 112 at a stage below the sixteenth stage via line 201. More preferably, the flow includes approximately 98.31% by weight of water and negligible quantities of ethanolamine.

The stripped resultant product effluent from line 109 can be introduced to the drying column 112 above the second stage of the drying column at a feed rate of approximately 20,000 kg/hr to approximately 30,000 kg/hr. More preferably, the feed rate can be approximately 24,611 kg/hr. More preferably, the resultant product effluent from line 109 can be introduced at the ninth stage of the drying column 112. The drying column 112 can remove any water still present in the stripped resultant product effluent by evaporation of the remaining water. The water can leave the drying column 112 as a vapor via line 113. In some alternatives, the vapor can be added as a recycled water stream to the drying column 112 to ensure that no MEA, DEA or TEA leaves the drying column 112 together with the vapor. In some alternatives, water recovered from the drying column 112 via line 113 can be recycled for use in the ammonia absorber 110. In some alternatives, a portion of the water recovered from the drying column 112 via line 113 can also be recycled for use throughout the process 100 via line 114. The drying column 112 can be operated at a pressure of approximately 260 millibar (mbar) to approximately 280 mbar, and more preferably approximately 270 mbar to approximately 273 mbar. The drying column 112 can include a heat exchanger 201 and a condenser 205, where line 204 feeds material from the drying column 112 and recycles back to the condenser 205 through line 206. The condenser 205 can have a reflux ratio of approximately 0 to approximately 1, and more preferably a reflux ratio of 0.2. The condenser can keep the top stages of the drying column 112 at a temperature of approximately 55° C. to approximately 75° C., and more preferably approximately 66.7° C. to approximately 67° C. In some alternatives, the heat exchange can be a thermosiphon or a forced circuit reboiler. Traditionally, a reboiler 201 (e.g., heat exchanger), with a duty from approximately 7,000 kilowatts (kW) to approximately 9,500 kW, and more preferably approximately 7,483 kw to approximately 9,099 kw can keep the bottom stages of the drying column 112 at a temperature of approximately 140° C. to approximately 160° C. More preferably, the temperature range at the bottom stages of the drying column 112 can be approximately 149° C. to approximately 150° C.

The dehydrated resultant product stream from the drying column 112 containing approximately 0.01% by weight of water, ethanolamines and byproducts can be fed to the MEA column 116 via line 115 at a point between the top and bottom of the MEA column 116. The flow rate of the dehydrated resultant product stream can be approximately 14,780 kg/hr to approximately 14,820 kg/hr, and more preferably, approximately 14,798 kg/hr. In some alternatives, the MEA distillation column 116 can contain thirteen stages. In some alternatives, the ethanolamine product stream can be fed at the seventh stage 208 of the MEA distillation column 116. The MEA distillation column 116 can be operated at a pressure of approximately 75 mbar to approximately 86 mbar, and more preferably from approximately 80 mbar to approximately 82 mbar. The MEA column 116 can be operated at a temperature of approximately 80° C. to approximately 160° C., and more preferably approximately 104.3° C. to approximately 144° C. Traditionally, a condenser 205 with a duty from approximately 1,200 kW to approximately 1,600 kW, and more preferably, approximately 1,480 kW can keep the top stages of the MEA column 116 at a temperature of approximately 80° C. to approximately 150° C., and more preferably, approximately 104.3° C. to approximately 104.5° C. In some alternatives, the heat exchanger 201 can be a thermosiphon or a forced circuit reboiler. Traditionally, a reboiler 201, with a duty of approximately 1,000 kW to approximately 1,500 kW, and more preferably, at approximately 1,252 kW can keep the bottom stages of the MEA column 116 at a temperature of approximately 140° C. to approximately 160° C. More preferably, the temperature range at the bottom stages of the MEA column 116 can be approximately 144° C. The MEA distillation column 116 can be operated at a reflux ratio of approximately 0.3 to approximately 0.6, and more preferably approximately 0.47 to approximately 0.5. A stream, which can contain ethanolamines, and byproducts can be collected at the bottom of the MEA distillation column 116, for example, at the thirteenth stage 210, and fed to a reboiler 201 via line 202. MEA can be distilled and returned to the MEA distillation column 116 via line 203. The DEA-TEA rich stream can exit the heat exchanger 201 via line 118 for further processing by the DEA columns 119, 122 and TEA column 125. The flow rate of the MEA collected from line 117 can be approximately 4,200 kg/hr to approximately 4,300 kg/hr, more preferably, approximately, 4,250 kg/hr. In some alternatives, the MEA collected from line 117 can contain approximately 0.2% by weight of water to approximately 0.4% by weight of water, and more preferably, approximately 0.3% by weight of water. In some alternatives, the ethanolamine product streams and the dummy stream can be recycled back to the reactor 105. Table 1 and Table 2 illustrate these results.

MEA product leaves MEA distillation column 116 through line 117, while the remaining feed in the MEA distillation column 116 is fed to the DEA splitter column 119 through line 118. DEA byproduct leaves the DEA splitter column 119 through line 120, while the remaining feed in the DEA splitter column 119 is fed to DEA distillation column 122 through line 121. DEA product leaves the DEA distillation column 122 through line 123, while the remaining feed in the DEA distillation column 122 is fed to the TEA distillation column 125 through line 124. TEA product leaves TEA distillation column 125 through line 126, while unreacted product and byproducts leave TEA distillation column 125 through line 127.

Example 2

Base Case at MEA Column 116 with Dummy Stream

The production of ethanolamines as described in Example 1 was further modeled to simulate adding a dummy stream at the MEA column 116. At the MEA column 116, a flow, which can contain approximately 99.99% by weight of water and negligible quantities of ethanolamines can be collected from the head of the MEA distillation column 116 via line 204 and can be condensed in heat exchanger 205. The resulting condensate, which can contain negligible quantities of ethanolamines, can in part be refluxed into the MEA distillation column 116 via line 206. The remainder of the condensate, which can contain approximately 2% by weight of water to approximately 4% by weight of water, and more preferably approximately 3.6% by weight of water, can be discharged as a dummy stream via line 207, near for example, at a first plate 209 of MEA distillation column 116. The dummy stream can include approximately 15 kg/hr of MEA to approximately 21 kg/hr of MEA, approximately 0.5 kg/hr of water to approximately 1% kg/hr of water, approximately 0.005% by weight of MEG to approximately 0.01% by weight of MEG and traces of TEA and DEA. More preferably, the dummy stream can include approximately 19.7 kg/hr of MEA, approximately 0.74 kg/hr of water, approximately 0.008% kg/hr of MEG and traces of TEA and DEA. The flow rate of the dummy stream via line 207 can be approximately 18 kg/hr to approximately 22 kg/hr, more preferably, approximately 20.5 kg/hr. A MEA product stream recovered from the MEA distillation column 116 can be collected via line 117. In some alternatives, the MEA collected from line 117 can contain reduced water content, than those from traditional ethanolamine production processes. In some alternatives, the MEA product stream can contain approximately 0.01% by weight of water to approximately 0.04% by weight of water, and more preferably, approximately 0.02% by weight of water. In some alternatives, the ethanolamine product streams and the dummy stream can be recycled back to the reactor 105. Table 1 and Table 2 illustrate these results.

Example 3

110% of Base Case at MEA Column 116

The production of ethanolamines as described in Example 1 was further modeled to simulate increased processing conditions at the MEA column 116. The processing conditions data at the MEA column 116 was increased by approximately 5% to approximately 20% over the base case data, and more preferably by approximately 10%. The processing conditions include, but are not limited to flow rates of the dehydrated product effluent, condenser heat duty, reboiler heat duty, and bottom flow rate of the MEA column 116. This simulation was labeled as 110% of base case.

The dehydrated resultant product stream from the drying column 112 containing approximately 0.01% by weight of water, ethanolamines and byproducts can be fed to the seventh stage 208 of the MEA column 116 via line 115. The MEA distillation column 116 can be operated at a pressure from approximately 80 mbar to approximately 82 mbar. Millibar as described herein refers to absolute pressure. The MEA column 116 can be operated at a temperature of approximately 102.7° C. to approximately 131.7° C. A condenser 205 with a duty of approximately 2,251 kW to approximately 2,254 kW can keep the top stages of the MEA column 116 at a temperature range of approximately 80° C. to approximately 150° C., and more preferably approximately 102.7° C. to approximately 104.3° C. A reboiler 201, with a duty of approximately 1,852 kW can keep the bottom stages of the MEA column 116 at a temperature approximately 131.7° C. The MEA distillation column 116 can be operated at a reflux ratio of approximately 0.47 to approximately 0.5. A stream, which can contain ethanolamines, and byproducts can be collected at the thirteenth stage 210 of the MEA distillation column 116, and fed to a reboiler 201 via line 202. MEA can be distilled and returned to the MEA distillation column 116 via line 203. The DEA-TEA rich stream can exit the heat exchange 201 via line 118 for further processing by the DEA columns 119, 122 and TEA column 125. The flow rate of the MEA collected from line 117 can be approximately 4,200 kg/hr to approximately 4,300 kg/hr, more preferably, approximately, 4,183 kg/hr to approximately 4,269 kg/hr. In some alternatives, the MEA product stream can contain approximately 0.1% by weight of water to approximately 0.3% by weight of water, and more preferably, approximately 0.19% by weight of water. In some alternatives, the ethanolamine product streams and the dummy stream can be recycled back to the reactor 105. Table 1 and Table 2 illustrate these results.

Example 4

110% of Base Case at MEA Column 116 with dummy stream

The production of ethanolamines as described in Example 3 was further modeled to simulate adding a dummy stream at the MEA column 116. At MEA column 116, a flow, which can contain approximately 99.99% by weight of water and negligible quantities of ethanolamines can be collected from the head of the MEA distillation column 116 via line 204 and can be condensed in the condenser 205. The resulting condensate, which can contain negligible quantities of ethanolamines, can in part be refluxed into the MEA distillation column 116 via line 206. The remainder of the condensate, which can contain approximately 7.8% by weight of water, can be discharged as a dummy stream via line 207, near for example, at the first plate 209 MEA distillation column 116 MEA. The dummy stream can include approximately 92.2% by weight of MEA, approximately 7.8% by weight of water, approximately 0.04% by weight of MEG and traces of TEA and DEA. The flow rate of the dummy stream via line 207 can be from approximately 70 kg/hr to approximately 100 kg/hr, more preferably, approximately 86 kg/hr. A MEA product stream recovered from the MEA distillation column 116 can be collected via line 117. The flow rate of the MEA collected from line 117 can be approximately 4,200 kg/hr to approximately 4,300 kg/hr, more preferably, approximately, 4,183 kg/hr. In some alternatives, the MEA collected from line 117 can contain approximately 0.03% by weight of water to approximately 0.06% by weight of water, and more preferably, approximately 0.04% by weight of water. In some alternatives, the ethanolamine product streams and dummy stream can be recycled back to the reactor 104. Table 1 and Table 2 illustrate these results.

Table 1 shows the output parameters at the MEA column 116. Temperature was measured in degrees Celsius (° C.), pressure in millibar (mbar) bottom rate in kilograms per hour (kg/hr), and heat duty in kilowatts (kW).

TABLE 1

Output Parameters at the MEA Column

| | | | MEA COLUMN 116 | | | | |
|---|---|---|---|---|---|---|---|
| Description | Units | Oxiteno PFD % | Simulated Base Case before adding Dummy | Simulated Base Case with Dummy | Simulated 110% Base Case before adding Dummy | Simulated 110% Base Case with Dummy | Actual plant production data |
| Load | % | 100 | 100 | 100 | 110 | 110 | 110 |
| Top Temp | ° C. | 104.9 | 104.3 | 104.5 | 102.7 | 104.3 | 105.2 |
| Pressure | mbar | 80 | 80 | 80 | 80 | 80 | 80 |
| Bottom Rate | kg/hr | 10548 | 10548 | 10548 | 12547 | 12547 | 12547 |
| Bottom Temp | ° C. | 144.8 | 144.0 | 144.0 | 131.7 | 131.7 | 139.8 |
| Pressure | mbar | 82 | 82 | 82 | 82 | 82 | 82 |
| Condenser Heat Duty, Qc | kW | 1723 | 1480 | 1480 | 2254 | 2251 | — |
| Reboiler Heat Duty, Qr | kW | 1252 | 1252 | 1252 | 1852 | 1852 | — |

Table 2 shows the comparison of the MEA product & water content for the simulated cases and for the actual plant production rate at the MEA column 116, where production was measured in kilograms her hour (kg/hr) and amount of each component was measured in weight percent (wt %).

TABLE 2

MEA Product and Water Content

| | | | MEA COLUMN 116 | | | | | | |
|---|---|---|---|---|---|---|---|---|---|
| Description | Units | Oxiteno PFD % | Simulated before adding Dummy | Simulated with Dummy | | Simulated 110% Base Case before adding Dummy | Simulated 110% Base Case with Dummy | | Actual plant production data |
| Load | % | 100 | 100 | 100 | | 110 | 110 | | 110 |
| Production | kg/h | MEA | MEA | MEA | Dummy | MEA | MEA | Dummy | MEA |
| | | 4250 | 4250 | 4230 | 20.5 | 4269 | 4183 | 86 | 4183 |
| H₂O | wt % | 0.03 | 0.03 | 0.02 | 3.6 | 0.19 | 0.04 | 7.8 | 0.15-0.19 |
| MEA | wt % | 99.68 | 99.7 | 99.6 | 96.3 | 99.7 | 99.6 | 92.2 | |
| DEA | wt % | 0 | 0 | 0 | 0 | 0 | 0 | 0 | 0 |
| TEA | wt % | 0 | 0 | 0 | 0 | 0 | 0 | 0 | 0 |
| MEG | wt % | 0.29 | 0.3 | 0.3 | 0.04 | 0.1 | 0.4 | 0.04 | |

Based on the results above, the amount of water present in the MEA product stream at the MEA column 116 can be reduced from approximately 0.02% to approximately 0.04% by weight of water by: (i) adding a dummy stream to the MEA column 116; and (ii) adjusting the processing conditions at the MEA column 116 by approximately 5% to approximately 20%, more preferably to approximately 10%. The increased processing conditions can result in an increase to the reboiler 202 duty, condenser 205 duty and the bottom stream flow rate of the MEA column 116. In some alternatives, the reboiler 202 duty can be increased from approximately 1,252 kW to approximately 1,852 kW, an increase of approximately 47.9%. In some alternatives, the bottom stream flow rate can be increased from approximately 10,548 kg/hr to approximately 12,547 kg/hr, an increase of approximately 18.9%. In some alternatives, the condenser 205 duty can be increased from approximately 1,480 kW to approximately 2,251 kW to approximately 2,254 kW, an increase in approximately 52.3%. In some alternatives, the increased reboiler 202 duty, condenser 205 duty and the bottom stream flow rate can play a significant role to minimize the amount of water in the ethanolamine product stream exiting the MEA column 116.

The MEA product stream from the actual plant can contain significantly more water than the simulations as a result of the imbalance in flow at the plant, i.e., the flow at the plant cannot be stable.

The method disclosed herein include(s) at least the following embodiments:

Embodiment 1: A method for producing an ethanolamine product stream in a non-reactive distillation column, comprising: mixing an ammonia solution comprising approximately 30% to approximately 40% by weight ammonia with ethylene oxide in a reactor to create a resultant product stream, wherein said resultant product stream comprises ethanolamines, unreacted ammonia and water; removing approximately 30% to approximately 50% by weight of the unreacted ammonia and approximately 50% to approximately 70% by weight of water from the resultant product stream to create a stripped product stream, wherein the stripped product stream comprises ethanolamines and approximately 30% to approximately 50% by weight of water; transferring the stripped product stream to at least one stage of a vacuum drying column to create a dehydrated product stream; transferring the dehydrated product stream to at least one stage of a monoethanolamine distillation column to create a distilled product stream, wherein the dehydrated product stream comprises ethanolamines and approximately 0.01% to approximately 0.1% by weight of water; operating the monoethanolamine distillation column at adjusted processing conditions, wherein said processing conditions are selected from the dehydrated product stream flow rate, reflux rate at the monoethanolamine distillation column, condenser heat duty at the monoethanolamine distillation column, reboiler heat duty at the monoethanolamine distillation column, bottom rate at the monoethanolamine distillation column, or a combination comprising at least one of the foregoing, and wherein said processing conditions are approximately 5% to approximately 20% above a base case value of the selected processing conditions; removing a portion of the water from the distilled product stream via a dummy stream to create an ethanolamine product stream, wherein said ethanolamine product stream comprises ethanolamines and approximately 0.02% to approximately 0.04% by weight of water.

Embodiment 2: The method of claim 1, wherein monoethanolamine is recovered from the ethanolamine product stream at the monoethanolamine distillation column.

Embodiment 3: The method of claim 1 or claim 2, wherein the ammonia solution comprises approximately 50% to approximately 70% by weight of water, approximately 1% to approximately 5% by weight of monoethanolamine, and approximately 1% to approximately 5% by weight of diethanolamine.

Embodiment 4: The method of claim 3, wherein the ammonia solution comprises approximately 33% by weight ammonia, approximately 62% by weight of water, approximately 2.7% of monoethanolamine, and approximately 2.2% of diethanolamine.

Embodiment 5: The method of any of claims 1-4, wherein the ethanolamines are selected from monoethanolamine, diethanolamine, triethanolamine, or a combination comprising at least one of the foregoing.

Embodiment 6: The method of any of claims 1-5, wherein the dummy stream comprises approximately 15 kilograms per hour to approximately 25 kilograms per hour of monoethanolamine, approximately 0.1 kilograms per hour to approximately 1.25 kilograms per hour of water, approximately 0.001 kilograms per hour to approximately 0.013 kilograms per hour of mono-ethylglycol and traces of diethanolamine and triethanolamine.

Embodiment 7: The method of claim 6, wherein the dummy stream comprises approximately 19.7 kilograms per hour of monoethanolamine, approximately 0.74 kilograms per hour of water, approximately 0.008% kilograms per hour of mono-ethylglycol and traces of diethanolamine and triethanolamine.

Embodiment 8: The method of any of claims 1-7, wherein the dummy stream flow rate is approximately 19 kilograms per hour to approximately 21 kilograms per hour.

Embodiment 9: The method of claim 8, wherein the dummy stream flow rate is approximately 20.5 kilograms per hour.

Embodiment 10: The method of any of claims 1-9, wherein the dummy stream exits the monoethanolamine distillation column at a temperature of approximately 65° C. to approximately 85° C.

Embodiment 11: The method of claim 10, wherein the dummy stream exits the monoethanolamine distillation column at a temperature of approximately 70.3° C. to approximately 81.9° C.

Embodiment 12: The method of any of claims 1-11, wherein the dummy stream exits the monoethanolamine distillation column at a pressure of approximately 70 millibar to approximately 90 millibar.

Embodiment 13: The method of claim 12, wherein the dummy stream exits the monoethanolamine distillation column at a pressure of approximately 80 millibar.

Embodiment 14: The method of any of claims 1-13, wherein the unreacted ammonia is recycled and added to the ammonia solution.

Embodiment 15: The method of any of claims 1-14, wherein the vacuum drying column is operated at a pressure of approximately 260 millibar to approximately 280 millibar and a temperature at top stages of the vacuum drying column of approximately 55° C. to approximately 75° C., and a temperature at bottom stages of the vacuum drying column of approximately 140° C. to approximately 160° C.

Embodiment 16: The method of any of claims 1-15, wherein the reactor is operated at a temperature of approximately 37° C. to approximately 70° C. and a pressure of approximately 15 barg to approximately 30 barg.

Embodiment 17: The method of any of claims 1-16, wherein the vacuum drying column comprises a heat exchanger selected from a thermosiphon, a reboiler, or a combination comprising at least one of the foregoing.

Embodiment 18: The method of any of claims 1-17, wherein the adjusted processing conditions are increased by 10%.

Embodiment 19: The method of any of claims 1-18, wherein the base case value comprises the dehydrated product stream at a flow rate of 14,798 kilograms per hour, a reflux rate of 1,508 kilograms per hour, a condenser heat duty of 1,480 kilowatts, a reboiler heat duty of 1,252 kilowatts, and a bottom rate of 10,548 kilograms per hour.

Embodiment 20: The method of any of claims 1-19, wherein the reactor comprises six stages.

Although the foregoing description is directed to the preferred embodiments of the invention, it is noted that other variation and modifications will be apparent to those skilled in the art, and may be made without departing from the spirit or scope of the invention. Moreover, features described in connection with one embodiment of the invention may be used in conjunction with other embodiments, even if not explicitly stated above.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for producing an ethanolamine product stream in a non-reactive distillation column, comprising:
    mixing an ammonia solution comprising 30% to 40% by weight ammonia with ethylene oxide in a reactor to create a resultant product stream, wherein said resultant product stream comprises ethanolamines, unreacted ammonia and water;
    removing 30% to 50% by weight of the unreacted ammonia and 50% to 70% by weight of water from the resultant product stream to create a stripped product stream, wherein the stripped product stream comprises ethanolamines and 30% to 50% by weight of water;
    transferring the stripped product stream to at least one stage of a vacuum drying column to create a dehydrated product stream;
    transferring the dehydrated product stream to at least one stage of a monoethanolamine distillation column to create a distilled product stream, wherein the dehydrated product stream comprises ethanolamines and 0.01% to 0.1% by weight of water;
    operating the monoethanolamine distillation column at adjusted processing conditions, wherein said processing conditions are selected from the dehydrated product stream flow rate, reflux rate at the monoethanolamine distillation column, condenser heat duty at the monoethanolamine distillation column, reboiler heat duty at the monoethanolamine distillation column, bottom rate at the monoethanolamine distillation column, or a combination comprising at least one of the foregoing, and wherein said processing conditions are 5% to 20% above a base case value of the selected processing conditions, wherein the base case value comprises the dehydrated product stream at a flow rate of 14,798 kilograms per hour, a reflux rate of 1,508 kilograms per hour, a condenser heat duty of 1,480 kilowatts, a reboiler heat duty of 1,252 kilowatts, and a bottom rate of 10,548 kilograms per hour;
    removing a portion of the water from the distilled product stream via a dummy stream to create an ethanolamine product stream, wherein said ethanolamine product stream comprises ethanolamines and 0.02% to 0.04% by weight of water.

2. The method of claim 1, wherein monoethanolamine is recovered from the ethanolamine product stream at the monoethanolamine distillation column.

3. The method of claim 1, wherein the ammonia solution comprises 50% to 70% by weight of water, 1% to 5% by weight of monoethanolamine, and 1% to 5% by weight of diethanolamine.

4. The method of claim 1, wherein the ethanolamines are selected from monoethanolamine, diethanolamine, triethanolamine, or a combination comprising at least one of the foregoing.

5. The method of claim 1, wherein the dummy stream comprises 15 kilograms per hour to 25 kilograms per hour of monoethanolamine, 0.1 kilograms per hour to 1.25 kilograms per hour of water, 0.001 kilograms per hour to 0.013 kilograms per hour of mono-ethylglycol and traces of diethanolamine and triethanolamine.

6. The method of claim 1, wherein the dummy stream flow rate is 19 kilograms per hour to 21 kilograms per hour.

7. The method of claim 1, wherein the dummy stream exits the monoethanolamine distillation column at a temperature of 70.3° C. to 81.9° C.

8. The method of claim 1, wherein the dummy stream exits the monoethanolamine distillation column at a pressure of 70 millibar to 90 millibar.

9. The method of claim 1, wherein the unreacted ammonia is recycled and added to the ammonia solution.

10. The method of claim 1, wherein the vacuum drying column is operated at a pressure of 260 millibar to 280 millibar and a temperature at top stages of the vacuum drying column of 55° C. to 75° C., and a temperature at bottom stages of the vacuum drying column of 140° C. to 160° C.

11. The method of claim 1, wherein the reactor is operated at a temperature of 37° C. to 70° C. and a pressure of 15 barg to 30 barg.

12. The method of claim 1, wherein the vacuum drying column comprises a heat exchanger selected from a thermosiphon, a reboiler, or a combination comprising at least one of the foregoing.

13. The method of claim 1, wherein the adjusted processing conditions are increased by 10%.

14. The method of claim 1, wherein the reactor comprises six stages.

15. The method of claim 1, wherein said processing conditions are selected from condenser heat duty at the monoethanolamine distillation column, reboiler heat duty at the monoethanolamine distillation column, or a combination comprising at least one of the foregoing.

16. The method of claim 15, wherein said processing conditions comprise a flow rate of the dehydrated product stream, the condenser heat duty at the monoethanolamine distillation column, the reboiler heat duty at the monoethanolamine distillation column, bottom rate at the monoethanolamine distillation column, and optionally reflux rate at the monoethanolamine distillation column.

17. A method for producing an ethanolamine product stream in a non-reactive distillation column, comprising:
mixing an ammonia solution comprising 30% to 40% by weight ammonia with ethylene oxide in a reactor to create a resultant product stream, wherein said resultant product stream comprises ethanolamines, unreacted ammonia and water;
removing 30% to 50% by weight of the unreacted ammonia and 50% to 70% by weight of water from the resultant product stream to create a stripped product stream, wherein the stripped product stream comprises ethanolamines and 30% to 50% by weight of water;
transferring the stripped product stream to at least one stage of a vacuum drying column to create a dehydrated product stream;
transferring the dehydrated product stream to at least one stage of a monoethanolamine distillation column to create a distilled product stream, wherein the dehydrated product stream comprises ethanolamines and 0.01% to 0.1% by weight of water;
operating the monoethanolamine distillation column at adjusted processing conditions, wherein said processing conditions are selected from the dehydrated product stream flow rate, reflux rate at the monoethanolamine distillation column, condenser heat duty at the monoethanolamine distillation column, reboiler heat duty at the monoethanolamine distillation column, bottom rate at the monoethanolamine distillation column, or a combination comprising at least one of the foregoing, and wherein said processing conditions are 5% to 20% above a base case value of the selected processing conditions; and
removing a portion of the water from the distilled product stream via a dummy stream to create an ethanolamine product stream, wherein said ethanolamine product stream comprises ethanolamines and 0.02% to 0.04% by weight of water,
wherein the base case value comprises
the dehydrated product stream at a flow rate of 14,780 kilograms per hour to 14,820 kilograms per hour,
a condenser heat duty of 1,200 kilowatts to 1,600 kilowatts, and
a reboiler heat duty of 1,000 kilowatts to 1,500 kilowatts.

18. The method of claim 17, wherein said processing conditions are selected from condenser heat duty at the monoethanolamine distillation column, reboiler heat duty at the monoethanolamine distillation column, or a combination comprising at least one of the foregoing.

19. The method of claim 18, wherein said processing conditions comprise a flow rate of the dehydrated product stream, the condenser heat duty at the monoethanolamine distillation column, the reboiler heat duty at the monoethanolamine distillation column, bottom rate at the monoethanolamine distillation column, and optionally reflux rate at the monoethanolamine distillation column.

* * * * *